United States Patent [19]

Sako et al.

[11] Patent Number: 4,857,329
[45] Date of Patent: Aug. 15, 1989

[54] PROCESS FOR EXTRACTING LIPIDS FROM MORTIERELLA GENUS FUNGI

[75] Inventors: Takeshi Sako; Toshihiro Yokochi; Masahito Sato; Osamu Suzuki; Toshikatsu Hakuta; Tsutomu Sugeta; Noriaki Nakazawa, all of Ibaraki, Japan

[73] Assignee: Agency of Industrial Science & Technology, Ibaraki, Japan

[21] Appl. No.: 891,912

[22] Filed: Aug. 1, 1986

[30] Foreign Application Priority Data

Aug. 19, 1985 [JP] Japan .................................. 60-181481

[51] Int. Cl.[4] .............................................. A61K 35/84
[52] U.S. Cl. .................................... 424/195.1; 514/558
[58] Field of Search ....................... 424/195.1; 514/558

[56] References Cited

U.S. PATENT DOCUMENTS 4,388,324  6/1983  Horrobin ...................... 514/282 X
4,393,049  7/1983  Horrobin ...................... 514/207 X

FOREIGN PATENT DOCUMENTS 0812291  3/1981  U.S.S.R. ........................... 424/195.1

OTHER PUBLICATIONS

Menor, Chem. Abs., 107, 178544w (1987).
Sako et al., Chem. Abs., 106, 174560e (1987).
Suzuki, Chem. Abs., 105, 4997q (1986).
Suzuki, Chem. Abs., 102, 219549u (1985).
Sako et al., "Yu Kagaku" (Oil Chemistry), vol. 35, No. 6, pp. 463–466, 1986.

Primary Examiner—John W. Rollins
Assistant Examiner—Wendy Catchpole
Attorney, Agent, or Firm—Armstrong, Nikaido, Marmelstein, Kubovcik & Murray

[57] ABSTRACT

Lipids containing gamma-linolenic acid are extracted from cells of Mortierella genus fungi by first grinding the cells in the presence or absence of a hot alcoholic solvent, and then extracting the alcohol-treated ground cells with a solvent in a supercritical state, or a mixture of a solvent in a supercritical state with a lower aliphatic alcohol or a lower aliphatic hydrocarbon.

15 Claims, No Drawings

PROCESS FOR EXTRACTING LIPIDS FROM MORTIERELLA GENUS FUNGI

BACKGROUND

This invention relates to a process for extracting valuable components from Mortierella genus fungi. More particularly, it relates to an industrially effective process for isolating valuable components such as γ-linolenic acid from Mortierella genus fungi.

There has been already proposed a process for the production of cells which have a high content of lipids containing γ-linolenic acid at a high density, which process comprises culturing Mortierella genus fungi such as Isabellina, Vinacea, Ramanniana, *Ramanniana var. anglispora* or Nana in a medium comprising carbohydrate(s) at a high concentration as carbon source(s).

In order to effectively isolate valuable components such as lipids containing γ-linolenic acid from the cells thus obtained in an industrial scale, it is required to develop an appropriate process for treating the cells.

Conventional processes for extracting valuable components from cells include the one which comprises using a mixture of chloroform and methanol and homogenizing the cells therein in the presence of, for example, glass beads thereby grinding the cells simultaneously with extracting lipids therefrom (cf. Japanese Patent Publication No. 58-22199).

However, the general process as described above is hardly available in an industrial scale since it is difficult to recover the employed glass beads and to use large-sized equipment. Further both of neutral and polar lipids can be eluted with the chloroform/methanol mixture, which makes it difficult to isolate and collect either of them. Thus this process has not been established yet as an industrially available one.

SUMMARY

It is an object of the present invention to provide an industrially effective process for extracting and isolating valuable components contained in Mortierella genus fungi therefrom.

THE PREFERRED EMBODIMENTS

According to the present invention, valuable components contained in Mortierella genus fungi can be extracted therefrom via the following steps (a) and (b):

(a) heating Mortierella genus fungi cells and grinding the same by applying a mechanical force thereto or grinding the same by applying a mechanical force thereto in an alcoholic solvent; and (b) extracting the valuable components from the ground Mortierella genus fungi cells with a solvent selected from among a solvent in a supercritical state, a solvent mixture of the solvent in a supercritical state and lower aliphatic alcohol(s) and a solvent mixture of the solvent in a supercritical state and lower aliphatic hydrocarbon(s).

The above step (a) is a pretreatment step wherein the cell walls of the Mortierella genus fungi are ground. The grinding may be performed by heating the Mortierella genus fungi cells and applying a mechanical force thereto or by applying a mechanical force thereto in an alcoholic solvent. A moisture-containing cell cake containing approximately 50 to 80% of moisture separated from a medium by centrifuging or filtering the same or a dried matter obtained therefrom may be used as the cells to be treated in this step. The former is preferable from an economical viewpoint. The cells may be heated in, for example, an autoclave preferably under a carbon dioxide atmosphere to prevent oxidation of the valuable components. Then the cells may be ground with a conventionally known device such as a ball mill, a friction disc mill or a Henschel mixer. The cells may be heated to a temperature of 150° to 200° C. The heating makes the cell walls of the cells fragile. Thus the grinding may be carried out for approximately 15 minutes to thereby give particles sufficiently fine for subjecting to the subsequent extraction.

On the other hand, it is required to grind unheated cells in an alcoholic solvent for a period of three hours or longer. Examples of the alcoholic solvent are lower aliphatic alcohols such as methanol, ethanol and propanol. Ethanol is preferable since it is safe to human beings.

This pretreatment affords the cells with the average radius of 0.1 mm or below, preferably approximately 0.01 to 0.05 mm.

Then the ground cells are subjected to an extraction step (b) wherein valuable components are extracted therefrom. The extraction may be carried out with the use of a solvent selected from among a solvent in a supercritical state, a solvent mixture of the solvent in a supercritical state and lower aliphatic alcohol(s) and a solvent mixture of the solvent in a supercritical state and lower saturated aliphatic hydrocarbon(s). The expression "solvent in a supercritical state" as used herein means a solvent in a state beyond its critical temperature and critical pressure and includes carbon dioxide and flon as well as hydrocarbons such as methane and ethane.

A solvent in a supercritical state can bring about a sufficient yield in extraction when employed alone. However the use of a mixture of the same with lower aliphatic alcohol(s) or lower aliphatic hydrocarbon(s) can bring about a remarkable increase in the yield. Examples of the lower aliphatic alcohols are those having a boiling point of 40° to 120° C., such as ethanol, propanol, isopropanol, butanol and isobutanol. Examples of the lower aliphatic hydrocarbons are butane, pentane, hexane, heptane and cyclohexane. These lower aliphatic alcohols or lower aliphatic hydrocarbons may be added in an amount of 0.05 to 0.3 part by weight, preferably 0.1 to 0.2 part by weight, per part by weight of the solvent in a supercritical state.

The extraction may be carried out by using a pressure container such as an autoclave at a temperature of 35° to 90° C., preferably 40° to 80° C. under a pressure of 200 to 600 kg/cm$^2$, preferably 300 to 500 kg/cm$^2$. Thus neutral lipids are mainly extracted and isolated from the ground cells.

As described above, the process of the present invention comprises a pretreatment step (a) wherein cell walls of the fungi are ground and an extraction step (b) wherein the ground cells are subjected to extraction with a solvent selected from among a solvent in a supercritical state, a solvent mixture of the solvent in a supercritical state and lower aliphatic alcohol(s) and a solvent mixture of the solvent in a supercritical state and lower aliphatic hydrocarbon(s). Thus neutral lipids can be efficiently extracted from the cells.

In particular, the grinding period can be significantly shortened by heating the cells to thereby make the cell walls fragile in the pretreatment step followed by grinding the cell walls.

Carbon dioxide is the most preferable solvent in a supercritical state since it is cheaper than conventional eluents for lipids, non-combustible and harmless to human beings. In addition, neutral lipids in the cells can be selectively eluted with carbon dioxide at a rate of approximately 100% and no polar lipid is substantially eluted thereby, which makes this solvent further suitable for the isolation and purification of lipids.

When the extraction is carried out with the use of a solvent in a supercritical state alone, the lipids can be isolated from the solvent by simply lowering the pressure at a definite temperature or elevating or lowering the temperature at a definite pressure. Therefore vacuum distillation for separating the lipids from the solvent is unnecessary.

When the extraction is carried out with the use of a solvent mixture of said solvent in a supercritical state and organic solvent(s) such as alcohols or hydrocarbons, the amount of the organic solvent(s) to be separated from the lipids is much smaller than in conventional liquid/liquid extraction, which brings about such an advantage that the energy cost required for the isolation can be significantly saved.

Now Examples of the present invention will be given.

EXAMPLE 1

Mortierella genus fungi were cultured on a large scale in a culture tank of 30 l in volume. The cells thus obtained were dehydrated by centrifuging to thereby give cells containing 50 to 70% of moisture. These cells were sterilized in an autoclave at 120° C. and 2 kg/cm$^2$ for ten minutes. The cells thus obtained, which will be referred to as original cells hereinafter, were subjected to the following pretreatment and extraction.

1.0 to 1.7 kg of the original cells were introduced into a stainless steel ball mill of 6 l in internal volume and 2 l of ethanol was added thereto. Then the cells were ground in the ball mill for three hours. After filtering the alcohol off, 20 g of the obtained cells, which will be referred to as pretreated cells A hereinafter, were introduced into a stainless steel autoclave of 300 ml in internal volume and extracted therein with the use of carbon dioxide as an eluent at 60° C. and 416 kg/cm$^2$ (Run No. 1) and 318 kg/cm$^2$ (Run No. 2). Table 1 shows the result of the extraction of lipids from the cells.

EXAMPLE 2

40 g of the pretreated cells A as described in Example 1 were introduced into the same autoclave as the one used in Example 1 and extracted therein with the use of a mixture, which was obtained by adding 10% by weight of n-hexane to carbon dioxide, as an eluent at 60° C. and 337 kg/cm$^2$ (Run No. 3) and 269 kg/cm$^2$ (Run No. 4). The result is also shown in Table 1.

EXAMPLE 3

50 g of the pretreated cells A as described in Example 1 were introduced in the same autoclave as the one used in Example 1 and extracted therein with the use of a solvent, which was obtained by adding 10% by weight of ethanol to carbon dioxide, as an eluent at 60° C. and 389 kg/cm$^2$ (Run No. 5) and 295 kg/cm$^2$ (Run No. 6). The result is also shown in Table 1.

EXAMPLE 4

The original cells as described in Example 1 were heated to 170° C. under a carbon dioxide atmosphere for approximately five minutes, introduced into a ball mill of 500 ml in internal volume and ground therein for 15 minutes without adding any ethanol. The cells thus obtained will be referred to as pretreated cells B hereinafter.

40 g of the pretreated cells B were introduced into the same autoclave as the one used in Example 1 and extracted therein with the use of a solvent, which was obtained by adding 10% by weight of n-hexane to carbon dioxide, at 60° C. and 475 kg/cm$^2$ (Run No. 7) and 389 kg/cm$^2$ (Run No. 8). The result is also shown in Table 1.

Table 1 suggests the following facts.

In Example 1, more than 85% by weight of the lipids contained in the cells could be collected by extracting at 60° C. and 416 kg/cm$^2$ (Run No. 1).

In Example 2, 85.3% of the lipids were collected by extracting at 60° C. and 337 kg/cm$^2$ (Run No. 3), which suggests that the addition of n-hexane to carbon dioxide remarkably enhanced the extracting capability of the eluent.

In Example 3, 91.0% of the lipids were collected by extracting at 60° C. and 389 kg/cm$^2$ (Run No. 5), which suggests that the addition of ethanol to carbon dioxide significantly enhanced the extracting capability of the eluent.

In Example 4, 82.3% of the lipids were collected by extracting at 60° C. and 475 kg/cm$^2$ (Run No. 7), almost similar to the case of Examples 1 and 2. Thus it has been revealed that the pretreatment employed in Example 4 could significantly shorten the grinding period of the cells without requiring any treatment for separating the solid (cells) from the liquid (ethanol).

TABLE 1

| Ex. No. | Run No. | Cells | | | | Extraction with supercritical carbon dioxide | | | | |
| --- | --- | --- | --- | --- | --- | --- | --- | --- | --- | --- |
| | | Wet weight (g) | Moisture content (%) | Dry weight (g) | Lipid content (%) | Pressure (Kg/cm$^2$) | Carbon dioxide (g) | Added n-hexane or ethanol (%) | Extract (g) | Yield (%) |
| 1 | 1 | 20.3 | 41.1 | 12.0 | 41.7 | 416 | 267 | — | 4.3 | 85.9 |
| | 2 | 20.3 | 41.1 | 12.0 | 41.7 | 318 | 251 | — | 2.9 | 58.0 |
| 2 | 3 | 40.5 | 41.1 | 23.9 | 41.7 | 337 | 254 | 9.6 | 8.5 | 85.3 |
| | 4 | 40.5 | 41.1 | 23.9 | 41.7 | 260 | 236 | 10.4 | 6.3 | 63.2 |
| 3 | 5 | 50.0 | 41.1 | 29.5 | 41.7 | 389 | 263 | 9.9 | 11.2 | 91.0 |
| | 6 | 50.0 | 41.1 | 29.5 | 41.7 | 295 | 245 | 10.6 | 9.5 | 77.2 |
| 4 | 7 | 40.0 | 44.2 | 22.3 | 55.0 | 475 | 275 | 9.3 | 10.1 | 82.3 |
| | 8 | 40.0 | 44.2 | 22.3 | 55.0 | 389 | 263 | 9.7 | 8.7 | 70.9 |

EXAMPLE 5

In order to study the usefulness of the extraction process according to the present invention, the lipid and fatty acid compositions of the extracts of Run Nos. 1, 3, 5 and 7 as shown in Table 1 were examined. The lipid composition of each extract was analyzed by thin layer chromatography combined with a densitometer. The fatty acid composition of each extract was analyzed by gas chromatography.

Tables 2 and 3 show the obtained results. Table 2 shows the lipid composition of each extract wherein each symbol has the following meaning:
TG: triglyceride, DG: diglyceride,
MG: monoglyceride, FFA: free fatty acid,
FS: free sterol and SE: sterol ester.

Table 3 shows the fatty acid composition of each extract
wherein each symbol has the following meaning:
14: 0—myristic acid,
16: 0—palmitic acid,
16: 1—palmitoleic acid,
18: 0—stearic acid,
18: 1—oleic acid,
18: 2—linoleic acid and
18: 3—γ-linolenic acid.

TABLE 2

| | Analysis of Lipid Composition | | | | | | | | | | | |
|---|---|---|---|---|---|---|---|---|---|---|---|---|
| RUN | Lipid composition of fed cells (%) | | | | | | Lipid composition of extracts (%) | | | | | |
| NO. | TG | DG | MG | FFA | FS | SE | TG | DG | MG | FFA | FS | SE |
| 1 | 84.1 | 11.7 | Tr | 0.1 | 0.9 | 2.4 | 84.1 | 9.9 | Tr | 2.2 | 1.5 | 2.3 |
| 3 | 84.1 | 11.7 | Tr | 0.1 | 0.9 | 2.4 | 85.1 | 8.6 | Tr | 1.9 | 1.2 | 3.2 |
| 5 | 84.1 | 11.7 | Tr | 0.1 | 0.9 | 2.4 | 85.3 | 10.9 | Tr | 2.9 | 0.9 | Tr |
| 7 | 64.3 | 17.7 | Tr | 12.3 | 4.2 | Tr | 62.5 | 16.9 | Tr | 14.6 | 4.8 | Tr |

Tr = trace

TABLE 3

| | Analysis of Fatty Acid Composition | | | | | | | | | | | | | |
|---|---|---|---|---|---|---|---|---|---|---|---|---|---|---|
| RUN | Fatty acid composition of fed cells (%) | | | | | | | Fatty acid composition of extracts (%) | | | | | | |
| NO. | 14:0 | 16:0 | 16:1 | 18:0 | 18:1 | 18:2 | 18:3 | 14:0 | 16:0 | 16:1 | 18:0 | 18:1 | 18:2 | 18:3 |
| 1 | 1.1 | 32.1 | 0.2 | 6.9 | 45.1 | 9.3 | 5.3 | 1.0 | 33.1 | Tr | 6.1 | 45.2 | 9.2 | 5.3 |
| 3 | 1.1 | 32.1 | 0.2 | 6.9 | 45.1 | 9.3 | 5.3 | 0.9 | 32.8 | Tr | 6.3 | 45.5 | 9.2 | 5.3 |
| 5 | 1.1 | 32.1 | 0.2 | 6.9 | 45.1 | 9.3 | 5.3 | 1.0 | 31.4 | 0.2 | 6.9 | 44.6 | 9.7 | 5.8 |
| 7 | 0.9 | 29.5 | 0.4 | 6.6 | 45.7 | 10.4 | 6.5 | 0.9 | 29.2 | 0.9 | 6.6 | 45.6 | 10.3 | 6.5 |

Tr = trace

The result as shown in Table 2 shows that free fatty acids tended to be selectively concentrated in each extract obtained by the extraction process according to the present invention with the use of supercritical carbon dioxide along or a solvent obtained by adding n-hexane or ethanol to the supercritical carbon dioxide and that the composition of other lipids in the extract was almost similar to that in the cells.

The result of the analysis of the extracts of Run Nos. 3, 5 and 7 obviously indicates that the addition of n-hexane or ethanol to the eluent or the heating treatment of the original cells hardly affected the composition of the lipid in the extracts. The triglyceride content by weight in the fed cells of Run No. 7 was lower than those of Run Nos. 1, 3 and 5. This was not caused by the fact that the heating in the pretreatment step accelerated the hydrolysis of triglyceride but by the fact that the moisture-containing cells obtained from a medium contained a lower amount of triglyceride (TG: 55.1% by weight).

In Examples 1, 2 and 3, each of the cells subjected to the extraction contained little polar lipids since most of the same migrated into the ethanol during the pretreatment step. On the other hand, the cells obtained from the pretreatment step in Example 4 contained approximately 4% of polar lipids. However, the extract obtained in Example 4 contained little polar lipids similar to those obtained in Examples 1, 2 and 3, which suggests that neutral lipids were selectively extracted by the process according to the present invention.

Table 3 shows the fatty acid composition of the extract obtained by Run Nos. 1, 3, 5 and 7. Every extract showed a fatty acid composition almost the same as that of the fed cells. The content of γ-linolenic acid in each extract was 5.3 to 6.5% by weight which is comparable to that of evening primrose oil. Thus it has been proven that the process of the present invention is effective in extracting lipids containing γ-linolenic acid from cells.

Accordingly it has been proven that the process for extraction with the use of a solvent in a supercritical state has various advantages such that it gives a high extraction efficiency, that the pretreatment step thereof can be readily carried out by simply grinding the cells and that it requires no special procedure for separating the valuable components from the solvent.

What is claimed is:

1. A process for extracting lipids from Mortierella genus fungi, which comprises the steps of:
   (a) heating Mortierella genus fungi cells and grinding the same by applying a mechanical force thereto or grinding the same by applying a mechanical force thereto in an alcoholic solvent; and
   (b) extracting the lipids from said Mortierella genus fungi cells thus ground with a solvent selected from the group consisting of a solvent in a supercritical state, a solvent mixture of said solvent in a supercritical state and a lower aliphatic alcohol and a solvent mixture of said solvent in a supercritical state and a lower saturated aliphatic hydrocarbon.

2. A process for extracting lipids from Mortierella genus fungi as set forth in claim 1, wherein the ground Mortierella genus fungi cells are a moisture-containing cell cake containing 50 to 80% of moisture.

3. A process for extracting lipids from Mortierella genus fungi as set forth in claim 1, wherein said cells are heated to 150° to 200° C.

4. A process for extracting lipids from Mortierella genus fungi as set forth in claim 1, wherein said alcoholic solvent is a lower aliphatic alcohol.

5. A process for extracting lipids from Mortierella genus fungi as set forth in claim 1, wherein the average particle radius of said ground cells is at most 0.1 mm.

6. A process for extracting lipids from Mortierella genus fungi as set forth in claim 1, wherein the average particle radius of said ground cells is 0.01 to 0.05 mm.

7. A process for extracting lipids from Mortierella genus fungi as set forth in claim 1, wherein said solvent in a supercritical state is carbon dioxide, flon, methane or ethane.

8. A process for extracting lipids from Mortierella genus fungi as set forth in claim 1, wherein said lower aliphatic alcohol is an aliphatic alcohol having a boiling point of 40° to 120° C.

9. A process for extracting lipids from Mortierella genus fungi as set forth in claim 1, wherein said lower aliphatic alcohol is an alcohol selected from the group consisting of ethanol, propanol, isopropanol, butanol and isobutanol.

10. A process for extracting lipids from Mortierella genus fungi as set forth in claim 1, wherein said lower aliphatic hydrocarbon is a hydrocarbon selected from the ground consisting of butane, pentane, hexane, heptane and cyclohexane.

11. A process for extracting lipids from Mortierella genus fungi as set forth in claim 1, wherein said lower aliphatic alcohol or said lower aliphatic hydrocarbon is added in an amount of 5 to 30% by weight based on said solvent in a supercritical state.

12. A process for extracting lipids from Mortierella genus fungi as set forth in claim 1, wherein said extraction is carried out at a temperature of 35° to 90° C.

13. A process for extracting lipids from Mortierella genus fungi as set forth in claim 1, wherein said extraction is carried out at a temperature of 40° to 80° C.

14. A process for extracting lipids from Mortierella genus fungi as set forth in claim 1, wherein said extraction is carried out under a pressure of 200 to 600 kg/cm$^2$.

15. A process for extracting lipids from Mortierella genus fungi as set forth in claim 1, wherein said extraction is carried out under a pressure of 300 to 500 kg/cm$^2$.

* * * * *